United States Patent [19]
Gray et al.

[11] Patent Number: 5,660,788
[45] Date of Patent: Aug. 26, 1997

[54] PROCESS FOR FORMING A APERTURED, THREE-DIMENSIONAL, MACROSCOPICALLY EXPANDED, PLASTIC WEB FOR ABSORBENT ARTICLES HAVING A TEXTURED WEARER-CONTACTING SURFACE

[75] Inventors: Brian F. Gray, Burlington; Michael J. Schettler, Barrie; Gregory Ashton, Markham, all of Canada

[73] Assignee: The Procter & Gamble Company, Cincinnati, Ohio

[21] Appl. No.: 478,077

[22] Filed: Jun. 7, 1995

Related U.S. Application Data

[62] Division of Ser. No. 154,661, Nov. 18, 1993.

[51] Int. Cl.$^6$ ............................................. B29C 67/00
[52] U.S. Cl. ......................................... 264/504; 427/180
[58] Field of Search ............................. 264/504, 131, 264/156; 425/290, 387.1, 388; 156/62.2, 252, 253, 308.2, 309.9; 428/131, 137; 427/180, 197, 198

[56] References Cited

U.S. PATENT DOCUMENTS

| | | | |
|---|---|---|---|
| 3,043,738 | 7/1962 | Demeter et al. | 156/229 |
| 3,077,882 | 2/1963 | Trewella | 128/156 |
| 3,081,515 | 3/1963 | Griswold et al. | 28/78 |
| 3,165,432 | 1/1965 | Plaskett | 156/244 |
| 3,190,781 | 6/1965 | Metz, Jr. | 156/244 |
| 3,331,728 | 7/1967 | Lane | 161/112 |
| 3,421,964 | 1/1969 | Arbit | 156/244 |
| 3,523,149 | 8/1970 | Hartmann | 264/90 |
| 3,878,014 | 4/1975 | Melead | 156/167 |
| 3,881,488 | 5/1975 | Delanty et al. | 128/287 |
| 3,911,186 | 10/1975 | Trotman | 428/137 |
| 3,917,501 | 11/1975 | Ferrucci et al. | 264/131 |
| 3,929,135 | 12/1975 | Thompson | 128/287 |
| 3,945,386 | 3/1976 | Anczurowski et al. | 128/287 |
| 3,965,906 | 6/1976 | Karami | 128/287 |
| 3,967,623 | 7/1976 | Butterworth et al. | 128/287 |
| 3,987,792 | 10/1976 | Hernandez et al. | 128/284 |
| 3,994,299 | 11/1976 | Karami | 128/287 |

(List continued on next page.)

FOREIGN PATENT DOCUMENTS

| | | | |
|---|---|---|---|
| 0 018684 | 11/1980 | European Pat. Off. | |
| 0 018 684 | 11/1980 | European Pat. Off. | |
| 0 040 084 | 11/1981 | European Pat. Off. | A61F 13/00 |
| 0 295 694 | 12/1988 | European Pat. Off. | B32B 27/12 |
| 0 409 535 A1 | 1/1991 | European Pat. Off. | D04H 11/08 |
| 0 545 423 A1 | 6/1993 | European Pat. Off. | A61F 13/15 |
| 57-191022 | 11/1982 | Japan | 264/131 |
| 2-193663 | 7/1990 | Japan | A61F 13/15 |
| 4-152945 | 5/1992 | Japan | A61F 13/15 |
| 5-137752 | 6/1993 | Japan | A61F 13/15 |
| 982757 | 2/1965 | United Kingdom. | |
| WO93/09741 | 5/1993 | WIPO | A61F 13/15 |
| WO93/12749 | 7/1993 | WIPO. | |
| WO93/22995 | 11/1993 | WIPO | A61F 13/15 |
| WO94/24354 | 11/1994 | WIPO. | |

*Primary Examiner*—Catherine Timm
*Attorney, Agent, or Firm*—Kevin C. Johnson; William Scott Andes; E. Kelly Linman

[57] ABSTRACT

A fluid pervious topsheet suitable for use on an absorbent article is disclosed. The topsheet includes an apertured, three-dimensional, macroscopically expanded, fluid pervious web having a textured wearer-contacting surface. The composite web permits liquids to penetrate while providing an improved, less plastic-like feel and visual aesthetics. The process of the present invention, in one embodiment, comprises extruding a polymeric film onto a forming structure, applying a pneumatic pressure to the film to cause the film to be urged into substantial conformance with the forming structure, and depositing a particulate material on said film while the film is in a semi-molten state. In another embodiment, the process of the present invention comprises extruding a polymeric film onto a forming structure, depositing a particulate material on the film while the film is in a semi-molten state to form a composite web, and applying a pneumatic pressure to the film to cause the film to be urged into substantial conformance with the forming structure.

1 Claim, 6 Drawing Sheets

U.S. PATENT DOCUMENTS

| | | | |
|---|---|---|---|
| 4,077,410 | 3/1978 | Butterworth et al. | 128/287 |
| 4,323,069 | 4/1982 | Ahr et al. | 128/287 |
| 4,342,314 | 8/1982 | Radel et al. | 128/287 |
| 4,463,045 | 7/1984 | Ahr | 604/370 |
| 4,609,518 | 9/1986 | Curro et al. | 264/504 |
| 4,619,724 | 10/1986 | Chatow | 156/72 |
| 4,622,036 | 11/1986 | Goodrum | 604/367 |
| 4,695,422 | 9/1987 | Curro et al. | 264/504 |
| 4,726,976 | 2/1988 | Karami et al. | 428/137 |
| 4,741,877 | 5/1988 | Mullane, Jr. | 264/504 |
| 4,747,991 | 5/1988 | Bishop | 264/504 |
| 4,781,962 | 11/1988 | Zamarripa et al. | 428/138 |
| 4,797,246 | 1/1989 | Reinke et al. | 264/504 |
| 4,878,825 | 11/1989 | Mullane, Jr. | 264/504 |
| 4,985,023 | 1/1991 | Blank et al. | 604/360 |
| 4,995,930 | 2/1991 | Merz et al. | 156/209 |
| 5,019,062 | 5/1991 | Ryan et al. | 604/359 |
| 5,171,238 | 12/1992 | Kajander | 604/383 |
| 5,173,351 | 12/1992 | Ruppel et al. | 428/1.74 |
| 5,282,915 | 2/1994 | Westlake, Jr. | 156/243 |
| 5,368,909 | 11/1994 | Langdon et al. | 428/137 |
| 5,368,910 | 11/1994 | Langdon | 428/137 |
| 5,383,870 | 1/1995 | Takai et al. | 604/366 |
| 5,387,209 | 2/1995 | Yamamoto et al. | 604/366 |
| 5,514,308 | 5/1996 | Cohen et al. | 156/308.8 |

PROCESS FOR FORMING A APERTURED, THREE-DIMENSIONAL, MACROSCOPICALLY EXPANDED, PLASTIC WEB FOR ABSORBENT ARTICLES HAVING A TEXTURED WEARER-CONTACTING SURFACE

CROSS REFERENCE TO RELATED APPLICATION

This application is a division of application Ser. No. 08/154,661, filed on Nov. 18, 1993.

FIELD OF THE INVENTION

The present invention relates to absorbent articles such as sanitary napkins, pantiliners, disposal diapers, incontinent articles, and the like, and more particularly, the present invention relates to absorbent articles having an apertured, three-dimensional, macroscopically expanded, plastic web topsheet, the wearer contacting surface of which is textured.

BACKGROUND OF THE INVENTION

All manner and variety of absorbent articles configured for the absorption of bodily fluids are, of course, well known. Current types of absorbent articles include sanitary napkins, pantiliners, disposable diapers, and incontinent articles.

Macroscopically expanded, three-dimensional, apertured, films have been used as topsheets on such absorbent articles. As used herein, the term "macroscopically expanded", when used to describe three-dimensional, plastic webs, ribbons and films, refers to webs, ribbons and films, which have been caused to conform to the surface of a three-dimensional forming structure so that both surfaces thereof exhibit the three-dimensional pattern of the forming structure, the pattern being readily visible to the naked eye when the perpendicular distance between the viewer's eye and the plane of the web is about 12 inches.

One macroscopically expanded, three-dimensional, apertured plastic web which is particularly well suited to transferring fluid deposited on one surface thereof to its opposite surface and thereafter isolating the transferred fluid from the wearer's skin is disclosed in commonly assigned U.S. Pat. No. 3,929,135 issued to Thompson on Dec. 30, 1975, and hereby incorporated herein by reference. Thompson describes a macroscopically expanded, three-dimensional, topsheet comprised of liquid impermeable material, but provided with a pattern of tapered capillaries, the capillaries have a base opening in the plane of the topsheet contacting the wearer's body and an apex opening remote from the base opening of the topsheet, the apex opening being in intimate contact with the absorbent pad utilized in the disposable absorbent article. The Thompson topsheet allows for the free transfer of fluid from the wearer's body into the absorbent element of the device while inhibiting the reverse flow of these fluids. This provides a relatively much dryer surface in contact with the user than had previously been obtainable.

Another macroscopically expanded, three-dimensional, apertured plastic web well suited for use as a topsheet on absorbent articles such as sanitary napkins is disclosed in commonly assigned U.S. Pat. No. 4,342,314 issued to Radel et al. on Aug. 3, 1982, said patent being hereby incorporated herein by reference. The macroscopically expanded, three-dimensional plastic web disclosed in the Radel et al. patent exhibits a fiber-like appearance and tactile impression which has been favorably received by consumers when used as a wearer contacting surface.

While macroscopically expanded, three-dimensional, apertured plastic webs have achieved widespread commercial success when employed as topsheets on absorbent articles, some users are very reluctant to place a topsheet which they readily perceive as plastic in contact with their skin.

Accordingly, it is therefore an object of the present invention to provide a topsheet for an absorbent article having fluid handling characteristics comparable to those found in macroscopically expanded, three-dimensional, apertured plastic topsheets and an improved softer, less plastic-like look and feel.

SUMMARY OF THE INVENTION

The present invention relates to absorbent articles such as diapers, incontinent articles, sanitary napkins, and the like. More particularly, this invention relates to absorbent articles having a resilient, three-dimensional, macroscopically expanded, fluid pervious plastic web. The plastic web has a first surface and a second surfaces located in planes remote from one another. At least a portion of the first surface of the web has a particulate material secured thereto. The web includes a plurality of capillaries extending from the first surface to the second surface of the web. The capillaries are defined by a plurality of sidewall portions interconnected to one another intermediate the first and second surfaces of the web. The sidewall portions terminate in the second surface of the web. In a preferred embodiment, the sidewall portions also have a particulate material secured thereto. Preferably, the particulate material is talc.

The present invention also provides a process for forming an apertured, three-dimensional, macroscopically expanded web. A polymeric film is extruded onto a forming structure. The forming structure exhibits a macroscopic, three-dimensional, cross-section defined by a multiplicity of macroscopic apertures which place the opposed surface of the forming structure in fluid communication with one another. A pneumatic pressure is applied to the film to cause the film to be urged into substantially conformance with the macroscopic, three-dimensional, cross-section of the forming structure thereby forming a three-dimensional, macroscopically expanded formed web having first and second surfaces located in planes remote from one another. The formed web has a plurality of capillaries extending from the first surface to the second surface. The capillaries are defined by a plurality of sidewall portions interconnected to one another intermediate the first and second surfaces and terminate in the second surface. A particulate material, preferably talc, is then deposited on the film while the film is in a semi-molten state.

Alternatively, the particulate material may be applied to the web after it has been extruded, but prior to passing over the vacuum chamber.

BRIEF DESCRIPTION OF THE DRAWINGS

While the specification concludes with claims particularly pointing out and distinctly claiming the present invention, it is believed that the present invention will be better understood from the following description in conjunction with the accompanying drawings in which:

DETAILED DESCRIPTION OF THE PRESENT INVENTION

The term "absorbent article", as used herein, refers to articles which absorb and contain body exudates. More specifically, the term refers to articles which are placed against or in proximity to the body of the wearer to absorb and contain the various exudates discharged from the body. The term "absorbent article:" is intended to include diapers, incontinent articles, sanitary napkins, pantiliners, and other articles used to absorb body exudates. The term "disposable " is used herein to describe absorbent articles which are not intended to be laundered or otherwise restored or reused as an absorbent article, i.e., they are intended to be discard after a single use, and, preferably to be recycled, composted or otherwise disposed of in an environmentally compatible manner.

The term "diaper" refers to a garment generally worn by infants and incontinent persons which is worn about the lower torso of the wearer. Suitable diapers that can be provided with the topsheet described herein are disclosed in U.S. Pat. No. Re. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986, U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany et al. on May 30, 1989; U.S. Pat. No. 4,888,231 issued to Angstadt on Dec. 19, 1989; and U.S. Pat. No. 4, 909,803 issued to Aziz, et al. on Mar. 20, 1990; each of which is incorporated herein by reference.

The term "incontinent article" refers to pads, undergarments (pads held in place by a suspension system of some type, such as a belt, or the like), inserts for absorbent articles, capacity boosters for absorbent articles, briefs, bed pads, and the like, regardless of whether they are worn by adults or other incontinent persons. Suitable incontinent articles that can be provided with the topsheet described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat No. 4,704, 115; U.S. Pat. No. 4,909,802 issued to Ahr, et al.; and U.S. Pat. No. 4,964,860 issued to Gipson, et al. on Oct. 23, 1990; each of which is incorporated herein by reference. The term "sanitary napkin" refers to an article which is worn by females adjacent to the pudendal region that is intended to absorb and contain various exudates which are discharged from the body (e.g., blood, menses and urine). Suitable sanitary napkins that can be provided with the topsheet described herein are disclosed in U.S. Pat. No. 4,285,343, issued to McNair on Aug. 25, 1981; U.S. Pat. Nos. 4,589, 876 and 4,687,478 issued to Van Tilburg on May 20, 1986 and Aug. 18, 1987 respectively; U.S Pat. Nos. 4,917,697 and 5,007,906 issued to Osborn, et al. on Apr. 17, 1990 and Apr. 16, 1991, respectively; and U.S. Pat. Nos. 4,950,264 and 5,009,653 issued to Osborn on Aug. 21, 1990 and Apr. 23, 1991,respectively; each of which is incorporated herein by reference. The term "pantiliner" refers to absorbent articles that are less bulky than sanitary napkins which are generally worn by women between their menstrual periods. Suitable pantiliners that can be provided with the topsheet described herein are disclosed in U.S. Pat. No. 4,738,676 issued to Osborn on Apr. 19, 1988.

Figure 1:
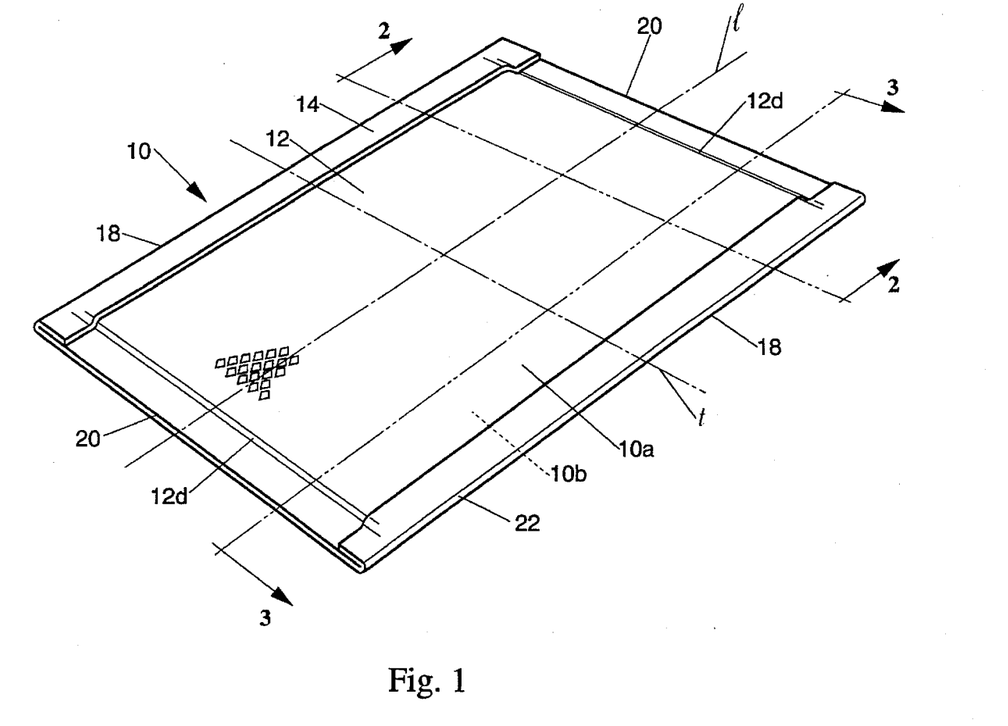
FIG. 1 is a simplified perspective view of an absorbent article of the present invention.
Figure 2:
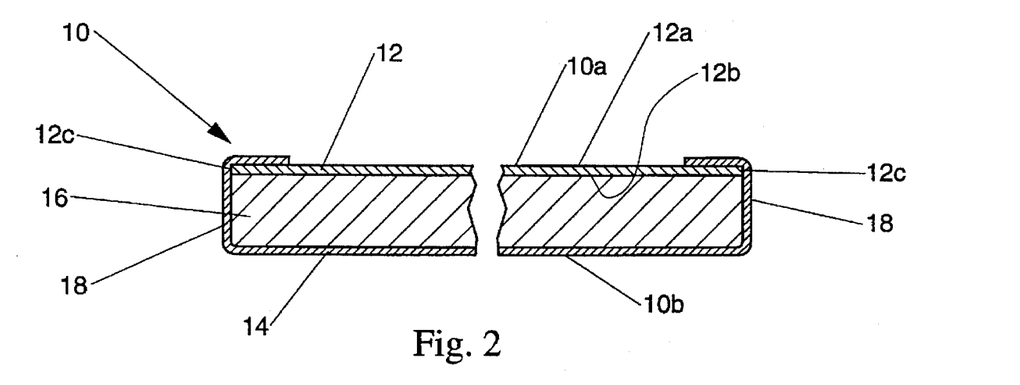
FIG. 2 is a cross-sectional view taken along section line 2—2 of FIG. 1.

FIG. 1 shows a simplified absorbent article 10 that could represent a diaper prior to its being placed on a wearer. It should be understood, however, that the present invention is not limited to the particular type or configuration of absorbent article shown in the drawings. As shown in FIG. 2, such an absorbent article 10 basically comprises a topsheet 12, a backsheet 14, and an absorbent core 16.

The absorbent article 10 has two surfaces, a body-contacting surface (or "body surface") 10a and a garment surface 10b. The body surface 10a is intended to be worn adjacent to the body of the wearer. The garment surface 10b of the absorbent article 10 (shown in FIG. 2) is on the opposite side and is intended to be placed adjacent to the wearer's undergarments or clothing when the absorbent article 10 is worn.

The absorbent article 10 has two centerlines, a longitudinal centerline 1 and a transverse centerline t. The term "longitudinal", as used herein, refers to a line, axis or direction in the plane of the absorbent article 10 that is generally aligned with (e.g., approximately parallel to) a vertical plane which bisects a standing wearer into left and right body halves when the absorbent article 10 is worn. The terms "transverse" or "lateral" as used herein, are interchangeable, and refer to a line, axis or direction which lies within the plane of the absorbent article 10 that is general perpendicular to the longitudinal direction. FIG. 1 shows that the absorbent article 10 has two spaced apart longitudinal edges 18 and two spaced apart transverse or end edges (or "ends") 20, which together form the periphery 22 of the absorbent article 10.

The topsheet 12 is compliant, sofa-feeling and non-irritating to the wearer's skin. Further, topsheet 12 is liquid permeable, permitting liquids to readily penetrate through its thickness. The topsheet 12 has a body-facing side or face 12a and a garment-facing side or face 12b, two longitudinal or side edges . 12c and two end edges 12d. (A similar numbering system will be used for the other components of the diaper 10. That is, the side of the component facing the wearer's body will be designated by the number of the component and a reference letter "a", the side facing the wearer's undergarments by the number of the component and the letter "b", and the side and end edges by the number of the component and the reference letters "c" and "d" respectively.)

Figure 4:
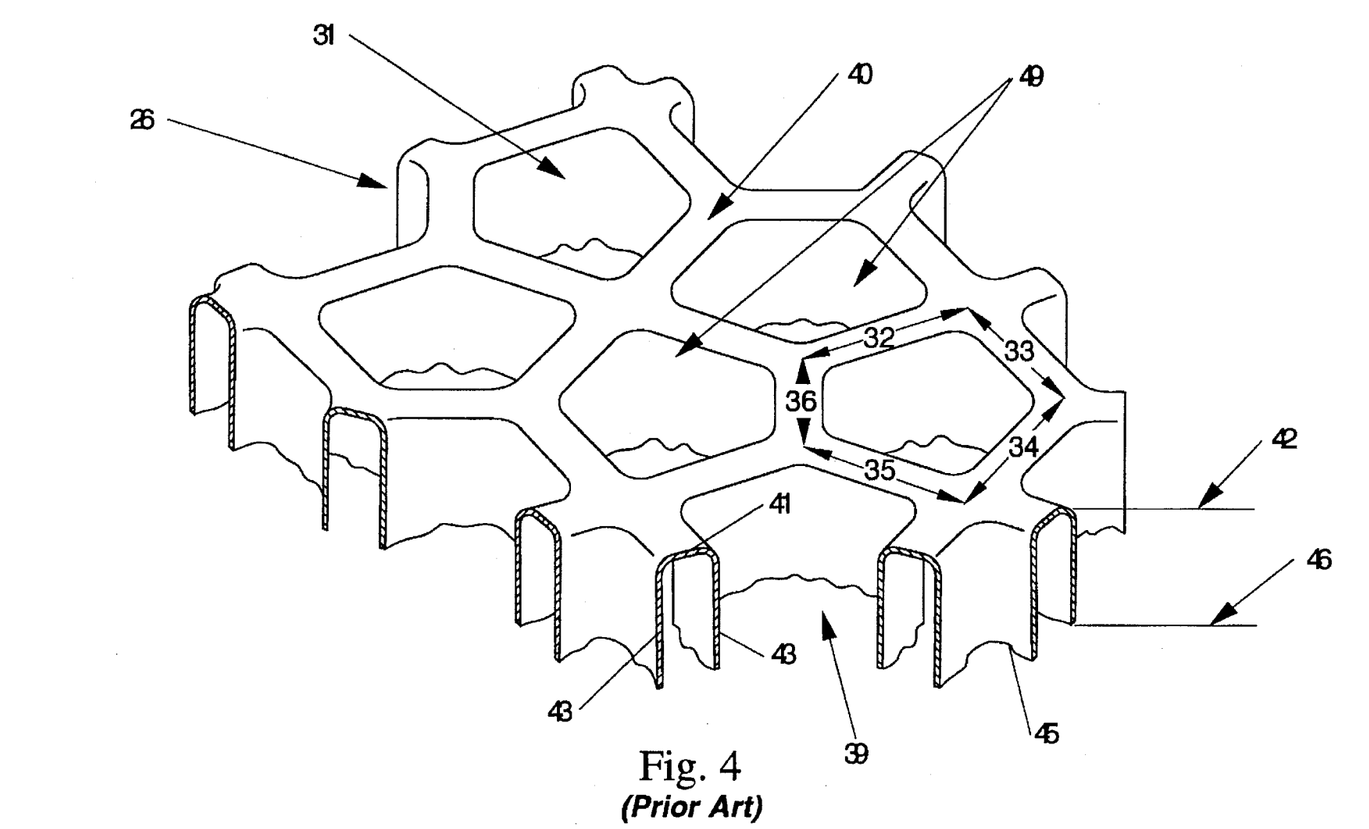
FIG. 4 is an enlarged, partially segmented, perspective illustration of a prior art plastic web of the type generally enclosed in commonly assigned U.S. Pat. No. 4,342,314.

FIG. 4 is an enlarged, partially segmented, perspective illustration of a prior art macroscopically expanded, three-dimensional, fiber-like, apertured, plastic film 26 which has been found highly suitable for use as a topsheet in disposal absorbent articles. Prior art plastic film 26 is generally in accordance with the teachings of commonly assigned U.S. Pat. No. 4,342,314 issued to Radel, et al. on Aug. 3, 1982 and is hereby incorporated herein by reference. The plastic film 26 exhibits a multiplicity of apertures, e.g., apertures 31, which are formed by a multiplicity of intersecting fiber-like elements, e.g., elements 32, 33, 34, 35 and 36 interconnected to one another in the first surface 40 of the web. Each fiber-like element comprises a base portion, e.g., base portion 41 located in plane 42. Each base portion has a sidewall portion, e.g., sidewall portions 43, attached to each edge thereof. The sidewall potions extend generally in the direction of a second surface 45 of the web. The intersecting sidewall portions of the fiber-like elements are interconnected to one another immediate the first and second surfaces of the web, and terminate substantially concurrently with one another in the plane 46 of the second surface to form apetures 39 in the second surface 45 of the web. The capillaries 49 formed by the interconnected sidewall portions allows for free transfer of fluid from the first surface of the web directly to the second surface of the web without lateral transmission of the fluid between the adjacent capillaries.

The apertured plastic film 26 is manufactured from a liquid impervious, preferably thermoplastic material. The thermoplastic material for use in the manufacture of the apertured formed plastic film 26 is selected from a group generally consisting of polyethylene, polypropylene, polyvinyl chloride, starch base resins, polyvinyl alcohol, polyurethanes, polycaprolactone cellulose esters and blends thereof.

Examples of other macroscopically expanded, three-dimensional, apertured, plastic webs are disclosed in U.S. Pat. No. 3,939,135 issued to Thompson on Dec. 30, 1975; U.S. Pat. No. 4,324,426, issued to Mullane, et al. on Apr. 13, 1982; and U.S. Pat. No. 4,463,045, issued to Ahr, et al on Jul. 31, 1984; each of said patents being hereby incorporated herein by reference.

Figure 5:
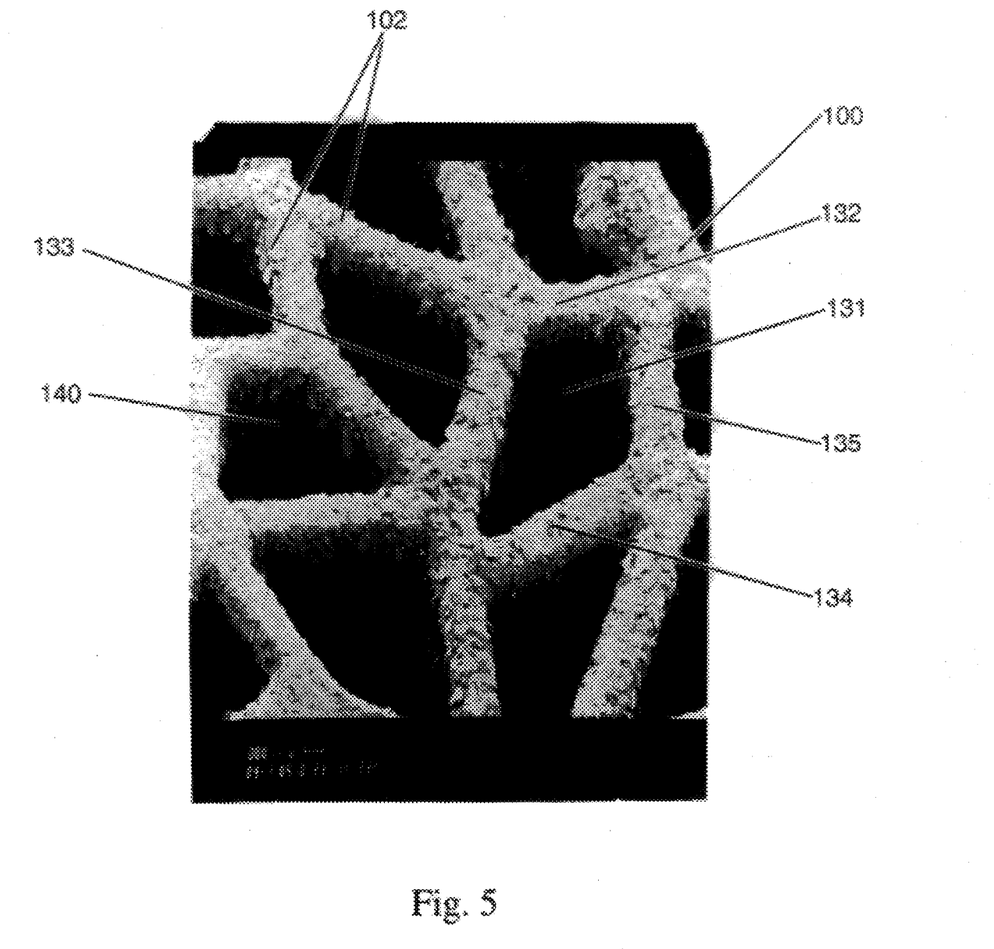
FIG. 5 is a photograph enlarged approximately 27 times of a preferred embodiment of an apertured, macroscopically expanded, three-dimensional, plastic web having a textured wearer-contacting surface of the present invention, the photograph being taken from the wearer-contacting surface of the web.

FIG. 5 is a photograph of an apertured, macroscopically expanded, three-dimensional, plastic web having a textured wearer-contacting surface, generally indicated as 100. Web 100 is particularly well suited for use as a topsheet, e.g., topsheet 12 illustrated in FIG. 1, on an absorbent article such as a diaper or sanitary napkin. The apertured, macroscopically expanded, three-dimensional, plastic web is generally in accordance with the teachings of commonly assigned U.S. Pat. No. 4,342,314 issued to Radel et al. The web 100 exhibits a multiplicity of apertures, e.g., apertures 131, which are formed by a multiplicity of intersecting fiber-like elements, e.g., elements 132, 133, 134, and 135 interconnected to one another in the first surface of the web. Each fiber-like element comprises a base portion located in the uppermost or wearer-contacting plane. Each base portion has a sidewall portion attached to each edge thereof. The sidewall portions extend generally in the directed of a second or absorbent core contacting surface of the web. The intersecting sidewall portions of the fiber-like elements are interconnected to one another intermediate the first and second surfaces of the web, and terminate substantially concurrently with one another in the plane of the second surface to form apertures in the second surface of the Web. The capillaries 140 formed by the interconnected sidewall portions allow for free transfer of fluid from the first of wearer-contacting surface of the web directly to the second or absorbent core contacting surface of the web without lateral transmission of fluid between adjacent capillaries.

Web 100 includes a particulate material 102 embedded on the wearer-contacting surface of the web and along the sidewall portions of the web. In a preferred embodiment the particulate material is talc. Another suitable particulate material is clay.

Preferably, the size of the particulate material 102 is such that light incident upon the visible surface of the web is substantially diffused into a multiplicity of directions by the particulate material into a multiplicity of directions rather than being specualry reflected, thereby providing a non-glossy visible surface.

Web 100 exhibits a soft, wearer-contacting surface which is not slick, sticky, or plastic-like when compared to prior art plastic films. The addition of the particulate material 102 to the first or wearer contacting surface of the apertured plastic film provides a textured surface which when utilized as a topsheet on an absorbent article is in contact with the wearer's skin. The addition of the particulate material to the wearer contacting surface of the apertured plastic film reduces the plastic,like feel often associated with such films which some users resist placing in contact with their skin.

In a particularly preferred embodiment, the particulate material is present when initially contacted by the wearer's skin in use. However, the particulate material is then "washed away" by the introduction of fluids (urine, menses, etc.). Therefore, the web 100 initially exhibits a sol, clothlike visual and tactile impression while presenting the after-use clean and dry benefits of prior art macroscopically expanded, three-dimensional, plastic webs. Depending on the desired results, the particulate material may be secured to the plastic web such that the particulate material is not "washed away" by the introduction of fluids.

Figure 6:
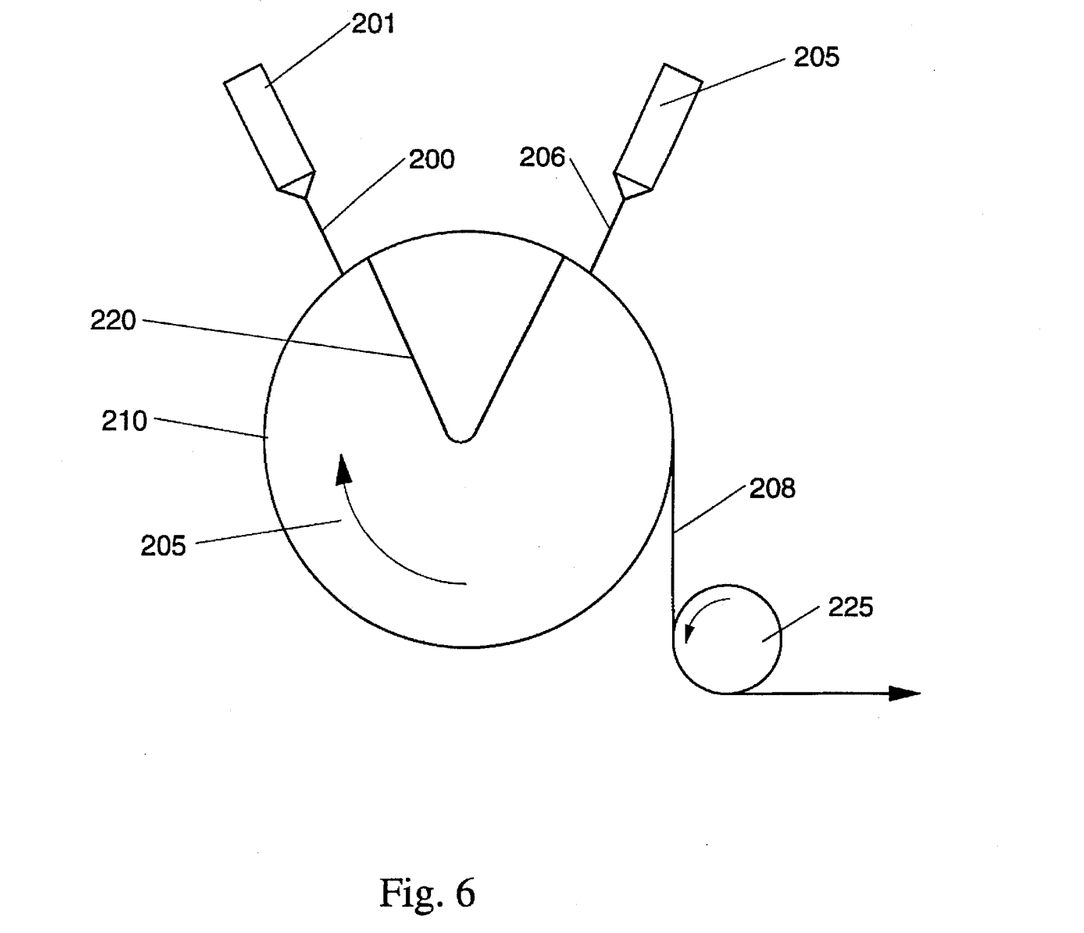
FIG. 6 is a simplified schematic representation of a process for making the apertured, macroscopically expanded, three-dimensional, plastic web having a textured wearer-contacting surface of the present invention.
Figure 7:
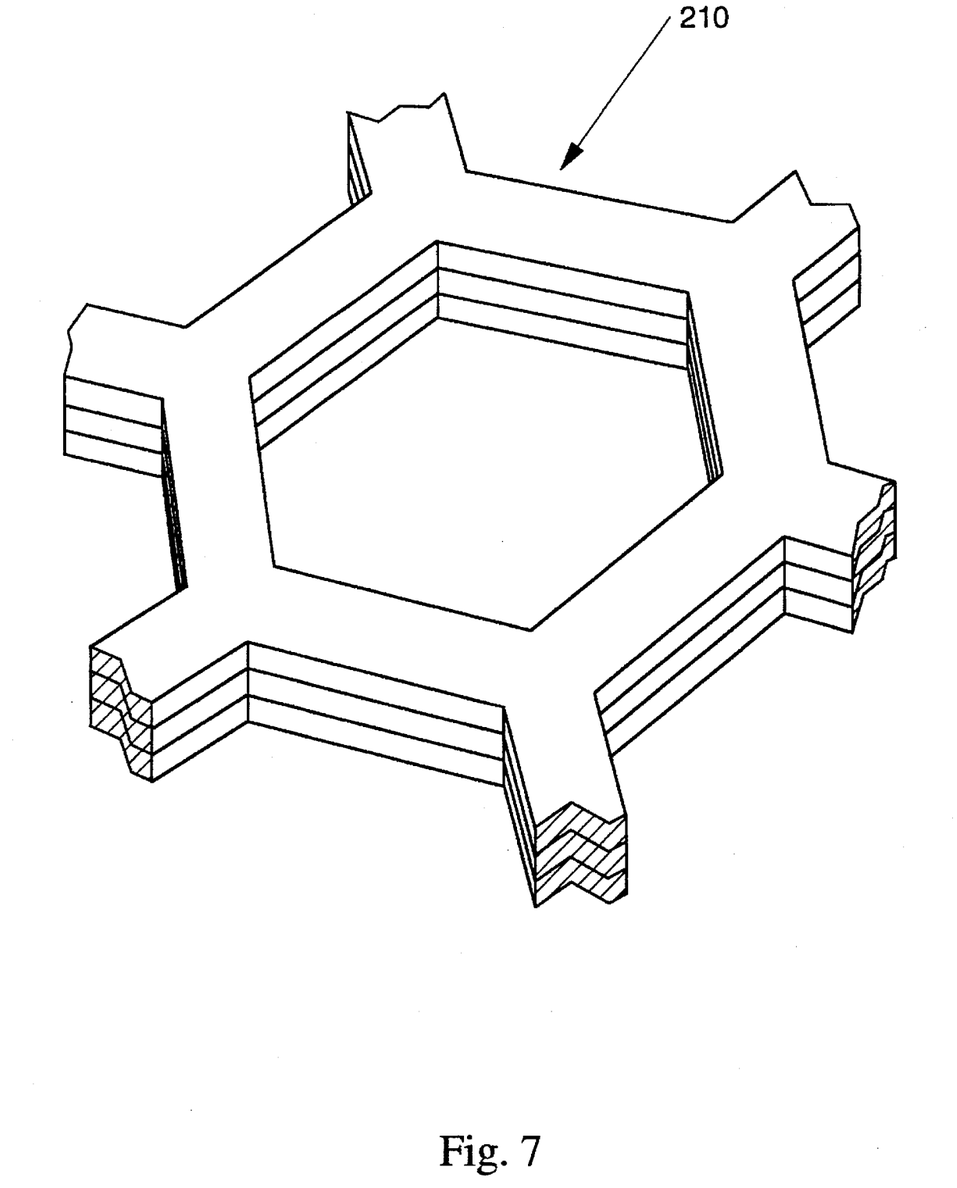
FIG. 7 is a greatly enlarged fragmentary illustration of a forming structure which may be utilized to support the web of the present invention in accordance with the process illustrated in FIG. 6.

A suitable process of preparing the web 100 of the present invention is shown in FIG. 6. In the embodiment shown in FIG. 6, a web of molten resin 200 is extruded from a conventional extruder 201 onto the surface of a forming drum 205 about which a forming structure 210 rotates. The forming drum 205 preferably includes an internally located vacuum chamber 220 which is preferably stationary relative to the moving forming structure 210. As the molten resin 200 passes across vacuum chamber 220 a pneumatic pressure is applied to the molten resin to cause the resin to be urged into substantial conformance with the forming structure 210. The macroscopic cross-section of forming structure 210 is visible in the greatly enlarged fragmentary perspective illustration of FIG. 7. Methods of constructing a suitable three-dimensional tubular forming member similar to that illustrated in FIG. 7 are disclosed in commonly assigned U.S. Pat. No. 4,508,256 issued to Radel et al. on Apr. 2, 1985 and commonly assigned U.S. Pat. No. 4,509,908 issued to Mullane, Jr. on Apr. 9, 1985, said patents being hereby incorporated herein by reference.

As the web of resin material conforms with the macroscopic cross-section of forming structure 210 a three-dimensional, macroscopically expanded, apertured web is created similar to that illustrated in FIG. 4. The web has a first surface and a second surface. The formed web includes a plurality of capillaries which extend from the first surface to the second surface. The capillaries are defined by a plurality of sidewall portions interconnected to one another intermediate the first and second surfaces and which terminate in the second surface of the web.

After having been formed by vacuum chamber 220, a particulate material 206 is applied to the semi-molten resin from applicator 205. The particulate material 206, preferably talc, readily adheres to the semi-molten resin to produce a web similar to that shown in FIG. 5.

After the particulate material has been secured to the apertured, plastic web, the resultant apertured, macroscopically expanded, three-dimensional, plastic web having a textured wearer-contacting surface 208 is removed from forming drum 210 by way of nip roll 225. The composite web 208 may be fed to a rewind station for temporary storage or may be utilized without further processing as a topsheet in an absorbent article.

Another suitable process for preparing the web 100 is by applying the particulate material to the extruded web of molten resin prior to the web crossing the vacuum chamber 220.

Yet, another suitable process for preparing the topsheet web 100 is by reheating a previously formed macroscopically expanded, three-dimensional, plastic web, to a semi-molten state prior to removing the web from the forming drum 205, such that the particulate material may be secured to the web.

Figure 3:
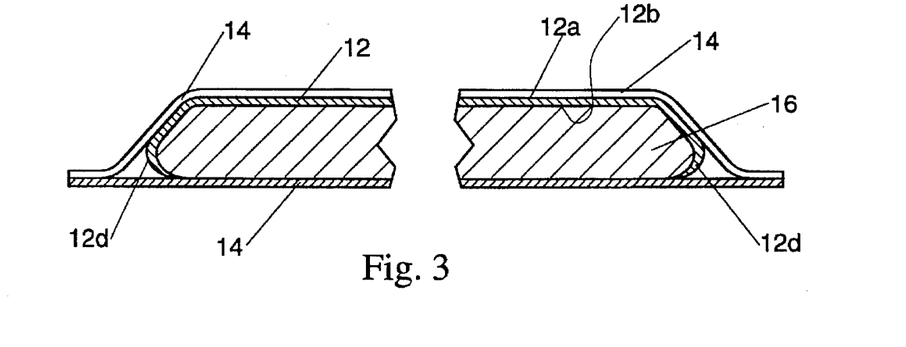
FIG. 3 is a cross-sectional view taken along section line 3—3 of FIG. 1.

The absorbent core 16 is positioned between the topsheet 12 and the backsheet 14. The absorbent core 16 may be any absorbent means which is capable of absorbing or retaining liquids (e.g.; menses and/or urine). As shown in FIGS. 1-3, the absorbent core 16 has a body surface, a garment surface, side edges and end edges. The absorbent core 16 may be manufactured in a wide variety of sizes and shapes (e.g., rectangular, oval, hour glass, dog bone, asymmetric, etc.) and from a wide variety of liquid-absorbent commonly used in absorbent articles such as comminuted wood pulp which is generally referred to as airfelt. Examples of other suitable materials include creped cellulose wadding, cross-linked cellulose fibers, absorbent foams, absorbent sponges, synthetic staple fibers, polymeric fibers, hydrogel-forming polymer gelling agents, peat moss, combinations of the foregoing, or any equivalent material or combinations of materials. The configuration and construction of the absorbent core may also be varied (e.g., the absorbent core may have varying caliber zones (e.g., profiled so as to be thicker in the center) hydrophilic gradients, super absorbent gradients, or lower density and lower average basis weight acquisition zones); or may comprise one or more layers or structures. The total absorbent capacity of the absorbent core should, however, be compatible with the desired loading and the intended use of the absorbent article. Further, the size and absorbent capacity of the absorbent core may be varied to accommodate different uses such as incontinence pads, pantiliners, regular sanitary napkins, or overnight sanitary napkins.

Suitable cross-linked cellulose fibers are described in U.S. Pat. No. 4,888,093, issued to Cook, et al. on Dec. 19, 1989; U.S. Pat. No. 4,822,543, issued to Dean, et al. on Apr. 18, 1989; U.S. Pat. No. 4,889,595, issued to Schoggen, et al. on Dec. 26, 1989; U.S. Pat. No. 4,889,596, issued to Schoggen, et al. on Dec. 26, 1989; U.S. Pat. No. 4,898,642 issued to Moore, et al. on Feb. 6, 1990; U.S. Pat. No. 4,935,022, issued to Lash, et al. on Jun. 19, 1990.

The characteristics of the absorbent core 16 for particular types of absorbent articles are described in greater detail in the patents and documents incorporated by reference herein, and the patents and other documents incorporated by reference herein. Other suitable absorbent core arrangements are described in U.S. Pat. Nos. 4,988,344 and 4,988,345, and European Patent Application Publication No. 0 198 683, published Oct. 22, 1986 in the name of Duenk, et al. which are also incorporated by reference herein. The absorbent article could also include any additional layers or other components such as are described in the patents incorporated by reference. For example, the absorbent article 10 may comprise an acquisition layer or patch or cross-linked cellulose fibers positioned between the topsheet 12 and the absorbent core 16.

The backsheet 14 and the topsheet 12 are positioned adjacent to the garment surface and the body surface, respectively, of the absorbent core 16 and are preferably joined thereto and to each other by attachment means (not shown) such as those well known in the art. For example, the backsheet 14 and/or the topsheet 12 may be secured to the absorbent core 16 by a uniform continuous layer of adhesive, a patterned layer of adhesive, or an array of separate lines, spirals, spots of adhesive, or meltblown adhesives. Adhesives which have been found to be satisfactory are manufacture by HB Fuller Company of St. Paul, Minnesota under the designation HL-1258. The attachment means will preferably comprise an open pattern network of filaments of adhesives as is disclosed in U.S. Pat. No. 4,573,986 issued to Minetola et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,91 1, 173 issued to Sprague, Jr. on Oct. 7, 1975; U.S. Pat. No. 4,785,996 issued to Zieker et al. on Nov. 22, 1978; and U.S. Pat. No. 4,842,666 issued to Werenicz on Jun. 27, 1989. Each of the patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 14 is impervious to liquids and is preferably manufactured from a thin plastic film, although other flexible liquid impervious materials may also be used. The backsheet 14 prevents liquid contained in absorbent core 16 from wetting articles which contact the absorbent article 10. Polyethylene films having a thickness of from about 0.001 to about 0.002 inches (0.0025 to 0.0051 cm.) have been used for the backsheet 14 with satisfactory results. As used herein, the term "flexible" refers to materials which are compliant and which will readily conform to the general shape and contours of the human body.

The backsheet 14 is superimposed on the garment-facing side 16b of absorbent core 16 and preferably extends beyond the edges thereof. The topsheet 12 is superimposed over the body-facing side 16a of the absorbent core 16, and may also extend beyond the edges of the core 16. The absorbent core 16 is, therefore, positioned between the topsheet 12 and the backsheet 14. The topsheet 12 and backsheet 14 are joined to each other such as around their peripheries. The topsheet 12 and backsheet 14 can be joined in any suitable manner such as by the use of adhesives, crimping, heat-sealing, or ultrasonic bonding.

While a number of particularly preferred embodiments in the present invention have been illustrated and described, it will be obvious to those skilled in the art that various changes and modifications can be made without the departing from the spirit and scope of the invention, and it is intended to the appended claims all such modifications that are in the scope of this invention.

What is claimed:

1. A process for forming an apertured, three-dimensional macroscopically expanded web, said process comprising the steps of:

(a) extruding a polymeric film onto a forming structure, said forming structure exhibiting a macroscopic, three-dimensional, cross-section defined by a multiplicity of macroscopic apertures which place opposed surfaces of said forming structure in fluid communication with one another;

(b) applying a pneumatic pressure to said film to cause said film to be urged into substantial conformance with the macroscopic three-dimensional, cross-section of said forming structure forming a three-dimensional, macroscopically expanded, formed web having first and second surfaces located in planes remote from one another, said formed web having a plurality of capillaries extending from said first surface to said second surface, said capillaries being defined by a plurality of sidewall portions interconnected to one another intermediate said first and second surfaces and terminating in said second surface; and (c) depositing a particulate material onto said first surface of said formed web and into said capillaries of said formed web along said sidewall portions while said formed web is in a semi-molten state, such that said particulate material is secured to said first surface and said sidewall portions of said formed web, wherein said particulate material is talc.

* * * * *